United States Patent [19]

Kropp

[11] Patent Number: 4,565,870
[45] Date of Patent: Jan. 21, 1986

[54] PROCESS FOR THE PREPARATION OF A SALT OF 1-(γ-HALOPROPYL)-1,2,3,4-β-CARBOLINES

[75] Inventor: Rudolf Kropp, Limburgerhof, Fed. Rep. of Germany

[73] Assignee: BASF Aktiengesellschaft, Fed. Rep. of Germany

[21] Appl. No.: 519,508

[22] Filed: Aug. 2, 1983

[30] Foreign Application Priority Data

Aug. 5, 1982 [DE] Fed. Rep. of Germany ....... 3229215

[51] Int. Cl.$^4$ ........................................... C07D 471/04
[52] U.S. Cl. ...................................... 546/85; 546/86; 546/87
[58] Field of Search ............................. 546/85, 86, 87

[56] References Cited

U.S. PATENT DOCUMENTS 2,786,059  3/1957  Horlein ................................. 546/87
3,304,309  2/1967  Shavel et al. ......................... 546/86

FOREIGN PATENT DOCUMENTS 0028381  10/1980  European Pat. Off. ............. 546/85

OTHER PUBLICATIONS

Chem. Abstracts, vol. 65, No. 3, p. 3844-c-e, Aug. 1, 1966.

Groves et al., Chem. Abstracts, vol. 46, No. 19, pp. 9569e-9571-d, Oct. 10, 1952.

Roger Adams, Ed., *Organic Reactions*, vol. VI, Chapter 3, "The Pictet-Spengler Synthesis of Tetrahydroisoquinolines and Related Compounds", (1951), pp. 151–187.

A. R. Katritsky, Ed., *Advances in Heterocyclic Chemistry*, vol. 3, "The Carbolines, III, Synthesis, A. Tetrahydrocarbolines", (1964), pp. 83–85.

*Primary Examiner*—Alan L. Rotman
*Attorney, Agent, or Firm*—Keil & Weinkauf

[57] ABSTRACT

Salts of 1,2,3,4-tetrahydro-β-carbolines of the formula I

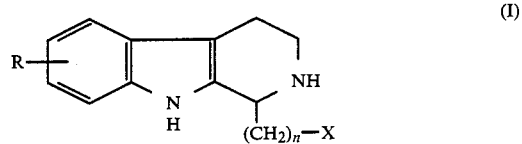

where R is hydrogen, halogen, $C_1$–$C_4$-alkyl, $C_1$–$C_4$-alkoxy or trifluoromethyl, x is halogen and n is an integer from 2 to 5, and their preparation are described. The compounds are intermediates for the preparation of pharmacologically active substances.

5 Claims, No Drawings

PROCESS FOR THE PREPARATION OF A SALT OF 1-(γ-HALOPROPYL)-1,2,3,4-β-CARBOLINES

The present invention relates to novel 1-(haloalkyl)-1,2,3,4-tetrahydro-β-carbolines, their preparation and their use for the production of pharmacologically important compounds.

It has been disclosed that tryptamine can be reacted with acetaldehyde to give 1-methyl-1,2,3,4-tetrahydro-β-carboline. However, this reaction cannot be successfully carried out with chlorinated acetaldehydes, such as chloral or chloroacetaldehyde (cf. Advances in Heterocyclic Chemistry 3 (1964), 83–85 and Organic Reactions 6 (1951), 151–187).

The present invention relates to salts of 1,2,3,4-tetrahydro-β-carbolines of the formula I

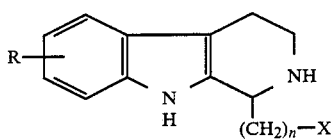

where R is hydrogen, halogen, $C_1$–$C_4$-alkyl, $C_1$–$C_4$-alkoxy or trifluoromethyl, X is halogen and n is an integer from 2 to 5.

Preferably, R is hydrogen, chlorine, bromine or trifluoromethyl, X is chlorine or bromine and n is 3 or 4. Preferred salts are those of inorganic acids, such as hydrohalic acids.

The salts of the novel compounds can be prepared by a process wherein a tryptamine of the formula II

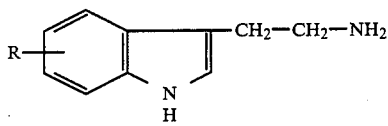

where R has the above meanings, is reacted with a haloaldehyde of the formula III

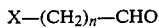

X—(CH$_2$)$_n$—CHO    III where X and n have the above meanings, or with an acetal of this compound, in the presence of an acid.

As described in Houben-Weyl, Volume 7/1, pages 285–290, the starting materials III can be readily prepared by catalytic hydrogenation of the corresponding acid chlorides.

The starting materials II are obtainable, for example by a Fischer indole synthesis, from unsubstituted or substituted arylhydrazines and γ-amino-, γ-halo- or γ-tosyloxyaldehydes or their acetals [Sundberg: The Chemistry of Indoles, page 228 (1970); The Chemistry of Heterocyclic Compounds: Indoles, Part II, page 22 (1972)].

Preferred starting materials II and III are those of the formulae where R is hydrogen, halogen, preferably chlorine or bromine, alkyl or alkoxy, each of 1 to 4 carbon atoms, or trifluoromethyl, and X is halogen, in particular chlorine or bromine. Suitable acetals of the compounds III are dialkyl acetals (preferably where alkyl is of not more than 4 carbon atoms) or cyclic acetals (preferably having 5 atoms in the ring).

The following tryptamines can be advantageously used as starting materials II: 3-(β-aminoethyl)-indole, 3-(β-aminoethyl)-5-methylindole, 3-(β-aminoethyl)-5-chloroindole, 3-(β-aminoethyl)-5-methoxyindole, 3-(β-aminoethyl)-6-trifluoromethylindole, 3-(β-aminoethyl)-7-methylindole and 3-(β-aminoethyl)-7-chloroindole and their salts, for example the hydrochlorides. Suitable starting materials III are β-chloropropionaldehyde, γ-chlorobutyraldehyde, δ-chlorovaleraldehyde, the corresponding bromo compounds and the dimethyl, diethyl and glycol acetals.

The starting materials and, where relevant, the acid are employed in the reaction in about stoichiometric amounts. The reaction is carried out in general at from 50° to 100° C., in particular from 70° to 120° C., under atmospheric or superatmospheric pressure, either continuously or batchwise. Advantageously a solvent which is inert under the reaction conditions is employed. Examples of suitable solvents are water, alcohols, such as methanol, ethanol and isopropanol, hydrocarbons, such as heptane, toluene and xylene, ethers, such as glycol monoethyl ether, tetrahydrofuran and dioxane, acetonitrile and dimethylformamide as well as mixtures of the stated solvents. The acid can be added to the reaction mixture, but it is also possible to react the compound II in the form of its salt.

The reaction can be carried out as follows: the starting materials, and if appropriate the solvent and the acid, are thoroughly mixed for from 1 to 10 hours at the reaction temperature. Where the reaction is carried out in a non-aqueous system, the product is obtained, during heating, in the form of its sparingly soluble salt, which can be filtered off under suction or separated off by centrifuging after the reaction mixture has cooled.

The course of the reaction is surprising since it was not to be expected that the preparation of the carbolines would take place successfully when chlorine-containing aldehydes were used.

The compounds in which n is 3 can be particularly advantageously prepared. In this case, the tryptamine can be replaced by the corresponding phenylhydrazine, which is reacted with 2 moles of halobutyraldehyde to give the carboline:

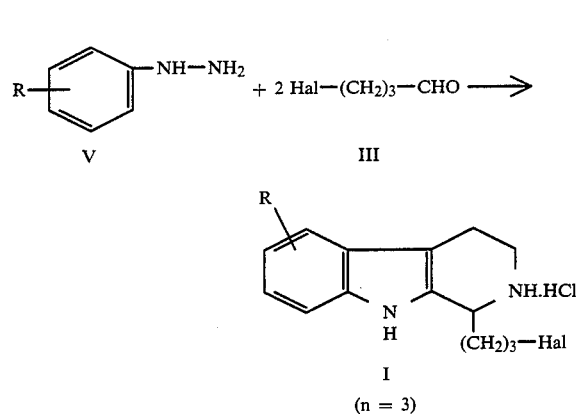

The starting materials are reacted with one another in about stoichiometric amounts, or an excess of one or other of the components is used; in general from 1.5 to 10, advantageously from 2 to 3, moles of starting material III are employed per mole of starting material V.

Examples of suitable hydrazines are phenylhydrazine, o-methylphenylhydrazine, p-isopropylphenylhydrazine, p-methylphenylhydrazine, p-ethylphenylhydrazine, m-trifluoromethylphenylhydrazine, p-chlorophenylhydrazine and o-bromophenylhydrazine.

Preferred starting materials III are γ-chlorobutyraldehyde and γ-bromobutyraldehyde.

The reaction is carried out in general at from 20° to 200° C., preferably from 60° to 120° C., under atmospheric or superatmospheric pressure, either continuously or batchwise. Advantageously, a solvent which is inert under the reaction conditions is used. Examples of suitable solvents are water, alcohols, such as methanol, ethanol and isopropanol, hydrocarbons, such as heptane, toluene and xylene, ethers, such as tetrahydrofuran and dioxane, acetonitrile and dimethylformamide as well as appropriate mixtures.

The reaction can be carried out as follows: a mixture of the starting materials and the solvent is kept at the reaction temperature for from 3 to 10 hours. Depending on the solvent used, the product crystallizes out during heating, during the subsequent cooling process or after the solvent has been evaporated off, and can be isolated by filtering it off under suction or by centrifuging. The product is a salt of 1-(halopropyl)-1,2,3,4-tetrahydro-β-carboline.

The novel compounds are useful intermediates for the preparation of 2-substituted 1-(3'-aminopropyl)-1,2,3,4-tetrahydro-β-carbolines of the formula IV

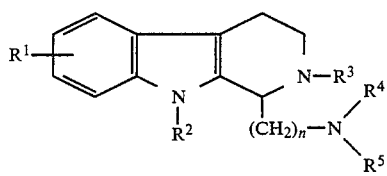

IV where n is an integer from 2 to 5, $R^1$ is hydrogen, halogen, trifluoromethyl, $C_1$-$C_4$-alkyl or $C_1$-$C_4$-alkoxy, $R^2$ is hydrogen or $C_1$-$C_3$-alkyl, $R^3$ is $C_1$-$C_3$-alkyl or $C_1$-$C_3$-acyl, $R^4$ is hydrogen or $C_1$-$C_4$-alkyl and $R^5$ is $C_1$-$C_4$-alkyl and, where $R^4$ is hydrogen, may furthermore be $C_1$-$C_4$-hydroxyalkyl or $C_2$-$C_4$-aminoalkyl in which the amine nitrogen atom can be substituted by $C_1$-$C_3$-alkyl or can form part of a 5-membered, 6-membered or 7-membered saturated ring which can contain another nitrogen atom or an oxygen atom as a further heteroatom, and any nitrogen atom present can be substituted by $C_1$-$C_3$-alkyl or $C_2$-$C_3$-hydroxyalkyl or by phenyl which is unsubstituted or monosubstituted by fluorine, chlorine, methoxy or methyl, or $R^4$ and $R^5$, together with the nitrogen atom, form a 5-membered, 6-membered or 7-membered saturated ring which can be substituted by one or more $C_1$-$C_3$-alkyl groups, a hydroxyl group and/or a phenyl group and can furthermore contain a nitrogen or oxygen atom as a further heteroatom, and any nitrogen atom present can be substituted by $C_1$-$C_3$-alkyl or $C_1$-$C_3$-hydroxyalkyl or by phenyl which is unsubstituted or monosubstituted by fluorine, chlorine, methoxy or methyl, and their salts with physiologically tolerated acids.

To prepare the compounds IV, a compound I is acylated at the N 2 atom with an acylating agent under trapping conditions in the presence of pyridine, in dimethylformamide, at from 0° to 15° C. If required, the alkyl radical $R^2$ can be introduced into this N 2-acylated compound by reacting the latter with the appropriate alkyl chloride or dialkyl sulfate in an inert solvent. The acyl radical at N 2 can then be converted to the alkyl group by reduction with lithium aluminum hydride in an inert solvent at from 50° to 100° C. The resulting compound of the formula V

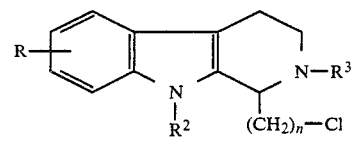

V is then reacted with an amine $HNR^4R^5$ in the presence of a tertiary amine, in tetrahydrofuran at from 0° to 150° C., to give IV.

The compounds IV are useful for the treatment of cardiovascular disorders and disorders of the central nervous system.

The Examples which follow illustrate the invention. Parts are by weight.

EXAMPLE 1

1-(γ-Chloropropyl)-1,2,3,4-tetrahydro-β-carboline (a) 1,280 parts of a 20.7% strength by weight solution of γ-chlorobutyraldehyde in xylene (prepared by a method similar to that described in Houben-Weyl, Volume 7/1, pages 285–290, by catalytic hydrogenation of a solution of γ-chlorobutyric acid chloride in xylene), 490 parts of 3-(β-aminoethyl)-indole hydrochloride and 1,000 parts of isopropanol were stirred for 4 hours at 88° C., and the mixture was cooled and then filtered under suction to give 618 parts (87%) of 1-(γ-chloropropyl)-1,2,3,4-tetrahydro-β-carboline hydrochloride. After recrystallization from methanol, the substance had a melting point of 219°–221° C.

(b) 950 parts of an 11.2% strength by weight solution of γ-chlorobutyraldehyde in xylene were stirred with 1,800 parts of isopropanol, 200 parts of water and 54 parts of phenylhydrazine for 6 hours at 80° C., after which about 2,000 parts of solvent were distilled off under reduced pressure from a waterpump, the residue was cooled and the product was filtered off under suction and washed with 200 parts of ethanol. 62 parts (43.5%) of 1-(γ-chloropropyl)-1,2,3,4-tetrahydro-β-carboline hydrochloride of melting point 216°–218° C. were obtained. After recrystallization from methanol, the substance had a melting point of 219°–221° C.

The following compounds were obtained by a method similar to that described in Example 1b:

1-(γ-Chloropropyl)-1,2,3,4-tetrahydro-6-methyl-β-carboline hydrochloride, mp.=204°–205° C., yield 36.8%;

1-(γ-Chloropropyl)-1,2,3,4-tetrahydro-6-chloro-β-carboline hydrochloride, mp.=235°–237° C., yield 40.6%.

EXAMPLE 2

1-(δ-Chlorobutyl)-1,2,3,4-tetrahydro-β-carboline 435 parts of a 13.7% strength by weight solution of δ-chlorovaleraldehyde in xylene (prepared by catalytic hydrogenation of a solution of δ-chlorovaleryl chloride in xylene) were stirred with 96 parts of 3-(β-aminoethyl)-indole hydrochloride in 500 parts of isopropanol for 6 hours at 85° C., and the mixture was cooled and then filtered under suction to give 92 parts (62.8%) of 1-(δ-chlorobutyl)-1,2,3,4-tetrahydro-β-carboline hydrochloride. After recrystallization, the substance had a melting point of 245°–247° C.

EXAMPLE 3

1-(γ-Chloropropyl)-1,2,3,4-tetrahydro-6-chloro-β-carboline 86 parts of a 17.5% strength by weight solution of γ-chlorobutyraldehyde in xylene, 33 parts of 3-β-aminoethyl)-5-chloroindole hydrochloride and 100 parts of isopropanol were stirred for 4 hours at 82° C., the mixture was cooled and the product was filtered off under suction and washed with 100 parts of isopropanol. 27 parts (59.4%) of 1-(γ-chloropropyl)-1,2,3,4-tetrahydro-6-chloro-β-carboline hydrochloride of melting point 234°–236° C. were obtained.

The substance was identical to the compound prepared similarly to Example 1.

EXAMPLE 4

1-(γ-Chloropropyl)-1,2,3,4-tetrahydro-β-carboline 200 parts of a 17.5% strength by weight solution of γ-chlorobutyraldehyde in xylene, 212 parts of isopropanol, 52 parts of 3-(β-aminoethyl)-indole and 388 parts of a 10% strength by weight aqueous sulfuric acid were stirred for 5 hours at 82° C., the mixture was cooled and the product was filtered off under suction and washed with 100 parts of isopropanol. 36 parts (31.6%) of 1-(γ-chloropropyl)-1,2,3,4-tetrahydro-β-carboline hydrochloride of melting point 216°–220° C. were obtained (cf. Example 1).

EXAMPLE 5

1-(γ-Chloropropyl)-1,2,3,4-tetrahydro-β-carboline 7 parts of γ-chlorobutyraldehyde diethyl acetal, 50 parts of isopropanol and 7.6 parts of 3-(β-aminoethyl)-indole hydrochloride were stirred for 7 hours at 83° C., and the mixture was cooled and then filtered under suction to give 5.5 parts (49.5%) of 1-(γ-chloropropyl)-1,2,3,4-tetrahydro-β-carboline hydrochloride of melting point 219°–221° C. The substance was identical to the product of Example 1.

We claim:

1. A process for the preparation of a salt of a compound of the formula I

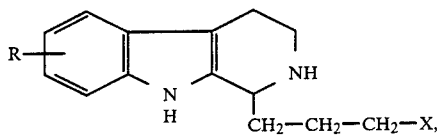

where R is hydrogen, halogen, $C_{1-4}$-alkyl, $C_{1-4}$-alkoxy, $CF_3$ and X is halogen which comprises: reacting a phenylhydrazine of the formula V

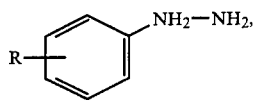

wherein R has the above meanings with a haloaldehyde of the formula III

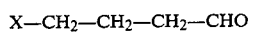

where X is halogen at a temperature of from about 50° to 150° C., and thereafter isolating the salt of the compound I.

2. The process of claim 1, wherein X is chlorine.
3. The process of claim 2, wherein R is hydrogen.
4. The process of claim 2, wherein R is chlorine.
5. The process of claim 2, wherein R is methyl.

* * * * *